US007179476B2

(12) United States Patent
Inagaki et al.

(10) Patent No.: US 7,179,476 B2
(45) Date of Patent: Feb. 20, 2007

(54) MEDICAL COMPOSITION FOR EXTERNAL USE FOR DERMATOSIS

(75) Inventors: Koji Inagaki, Mishima-gun (JP); Yoshiko Abe, Mishima-gun (JP); Kiyoshi Kuriyama, Mishima-gun (JP)

(73) Assignee: Sekisui Chemical Co., Ltd., Osaka (JP)

( * ) Notice: Subject to any disclaimer, the term of this patent is extended or adjusted under 35 U.S.C. 154(b) by 454 days.

(21) Appl. No.: 10/486,257

(22) PCT Filed: Aug. 9, 2002

(86) PCT No.: PCT/JP02/08160

§ 371 (c)(1),
(2), (4) Date: May 7, 2004

(87) PCT Pub. No.: WO03/013548

PCT Pub. Date: Feb. 20, 2003

(65) Prior Publication Data

US 2004/0213749 A1 Oct. 28, 2004

(30) Foreign Application Priority Data

Aug. 9, 2001 (JP) ............................. 2001-242464
Aug. 9, 2001 (JP) ............................. 2001-242466
Dec. 18, 2001 (JP) ............................. 2001-384942
Dec. 18, 2001 (JP) ............................. 2001-384943

(51) Int. Cl.
*A61K 6/00* (2006.01)
*A61K 31/35* (2006.01)
*A61K 8/02* (2006.01)

(52) U.S. Cl. ...................... 424/401; 514/456; 514/946

(58) Field of Classification Search ................ 424/401; 514/456, 946
See application file for complete search history.

(56) References Cited

U.S. PATENT DOCUMENTS

| 4,983,386 | A | * | 1/1991 | Kamishita et al. ....... 514/772.1 |
| 5,158,761 | A | * | 10/1992 | Kamishita et al. ............ 424/45 |
| 5,215,739 | A | * | 6/1993 | Kamishita et al. ............ 424/45 |
| 5,736,537 | A | * | 4/1998 | Gubernick et al. ......... 514/178 |
| 6,319,513 | B1 | * | 11/2001 | Dobrozsi ..................... 424/434 |
| 6,608,101 | B1 | * | 8/2003 | Ni et al. ..................... 514/443 |
| 6,987,120 | B1 | * | 1/2006 | Del Soldato ................ 514/365 |
| 2004/0213749 | A1 | * | 10/2004 | Inagaki et al. ............. 424/70.1 |

FOREIGN PATENT DOCUMENTS

| EP | 0 603 405 A1 | 6/1994 |
| GB | 52-44242 | 4/1977 |
| GB | 1537047 | 12/1978 |
| JP | 11-335281 A | 7/1999 |
| JP | 11-335282 A | 7/1999 |
| JP | 11-335282 A | 12/1999 |
| WO | 93/24129 A4 | 12/1993 |
| WO | WO 93/24129 A1 | 12/1993 |

OTHER PUBLICATIONS

Saleh et al., Effect of some drugs and additives . . . , (abstract only), International Journal of Pharmaceutics, vol. 57, Issue 3, Dec. 29, 1989, pp. 205-210.*

* cited by examiner

*Primary Examiner*—Vickie Kim
(74) *Attorney, Agent, or Firm*—Sughrue Mion, PLLC

(57) ABSTRACT

The object of the present invention is to provide a dermal composition for external use which keeps skin healthy and demonstrates a sufficient effect in treating skin diseases.

The present invention relates to a dermal composition for external use, which comprises sodium cromoglycate and a monoester of polyvalent alcohol and salicylic acid contained in a base.

12 Claims, No Drawings

MEDICAL COMPOSITION FOR EXTERNAL USE FOR DERMATOSIS

TECHNICAL FIELD

The present invention relates to a dermal composition for external use, which keeps skin healthy and demonstrates a sufficient effect in treating skin diseases.

BACKGROUND ART

Sodium cromoglycate (1,3-bis(2-carboxychromon-5-yloxy)-2-hydroxypropane sodium salt) is known as a substance for regulating release of chemical mediators from mast cells upon type I allergic reaction, and used in treatment of allergic diseases such as allergic asthma by administering inhalation capsules, inhalation solution or aerosol preparation thereof through inhalation. Japanese Kokai Publication Sho-52-44242 discloses that sodium cromoglycate is used in treatment of chronic skin diseases and eye diseases attributable to allergic or immune reaction by topical administration thereof into skin or optic tissues. Japanese Kokai Publication Hei-11-335281 and Japanese Kokai Publication Hei-11-335282 disclose that an external preparation containing sodium cromoglycate is effective in treatment of skin diseases such as dry skin.

However, the therapeutic effect of the external preparation containing sodium cromoglycate in treating skin diseases was not necessarily sufficient.

SUMMARY OF THE INVENTION

The object of the present invention is to provide a dermal composition for external use which keeps skin healthy and demonstrates a sufficient effect in treating skin diseases.

The present invention relates to a dermal composition for external use, which comprises sodium cromoglycate and a monoester of polyvalent alcohol and salicylic acid contained in a base. The monoester of polyvalent alcohol and salicylic acid is preferably glycol salicylate, and the content thereof is preferably 1 to 20% by weight. The base is preferably a water-soluble base.

Preferably, the dermal composition for external use of the present invention further contains at least one transcutaneous absorption enhancer selected from the group consisting of N-acyl sarcosine or a salt thereof, a higher fatty acid ester of a C10 to C18 higher fatty acid and a C1 to C20 alcohol, a C2 to C10 dicarboxylic acid or a salt thereof, a hydroxycarboxylic acid ester of a C3 to C6 hydroxycarboxylic acid and a C1 to C20 alcohol, fatty acid ethanol amide, glycerin, propylene glycol, polyethylene glycol, urea, glycyrrhizinic acid, squalane and mucopolysaccharide. The transcutaneous absorption enhancer is more preferably at least one member selected from the group consisting of glycerin, propylene glycol, urea, squalane and mucopolysaccharide.

The dermal composition for external use of the present invention has a pH value of preferably 2 to 7, more preferably 4 to 5.

DETAILED DISCLOSURE OF THE INVENTION

Hereinafter, the present invention is described in more detail.

The present inventors extensively studied the pharmacological action of sodium cromoglycate, and as a result they found that sodium cromoglycate is used in combination with a monoester of polyvalent alcohol and salicylic acid thereby significantly improving the effect of sodium cromoglycate in keeping skin healthy or in treating skin diseases, thus completing the present invention.

The dermal composition for external use of the present invention comprises sodium cromoglycate as the active ingredient and a monoester of polyvalent alcohol and salicylic acid contained in a base. It is estimated that the high therapeutic effect can be achieved by using sodium cromoglycate in combination with the monoester of polyvalent alcohol and salicylic acid.

The content of the above-mentioned sodium cromoglycate in the dermal composition for external use of the present invention is preferably 0.1 to 50% by weight. When the content is less than 0.1% by weight, the sufficient therapeutic effect may not be obtained, while when the content is higher than 50% by weight, the therapeutic effect is not significantly increased in proportion to the content, and there may also arise a problem in the pharmaceutical form. The content is more preferably 0.3 to 30% by weight, still more preferably 0.5 to 10% by weight.

The above-mentioned monoester of polyvalent alcohol and salicylic acid is an ester as a reaction product of one molecule of polyvalent alcohol and one molecule of salicylic acid, and examples thereof include glycol salicylate (ethylene glycol salicylate), propylene glycol salicylate, and glycerin salicylic monoester. In particular, glycol salicylate is preferable.

The content of the monoester of polyvalent alcohol and salicylic aid in the dermal composition for external use of the present invention is preferably 0.1 to 50% by weight. When the content is less than 0.1% by weight, the promoting effect on transcutaneous absorption may be insufficient, while when the content is higher than 50% by weight, the therapeutic effect is not significantly increased in proportion to the content, and there may also arise a problem in the pharmaceutical form. The content is more preferably 0.5 to 30% by weight, still more preferably 1 to 20% by weight.

Preferably, the dermal composition for external use of the present invention further comprises another transcutaneous absorption enhancer. The transcutaneous absorption enhancer is preferably at least one member selected from the group consisting of N-acyl sarcosine or a salt thereof, a higher fatty acid ester of a C10 to C18 higher fatty acid and a C1 to C20 alcohol, a C2 to C10 dicarboxylic acid or a salt thereof, a hydroxycarboxylic acid ester of a C3 to C6 hydroxycarboxylic acid and a C1 to C20 alcohol, a fatty acid ethanol amide, glycerin, propylene glycol, polyethylene glycol, urea, glycyrrhizinic acid, squalane and mucopolysaccharide.

The N-acyl sarcosine includes, for example, N-lauroyl sarcosine, N-oleoyl sarcosine, N-palmitoyl sarcosine and palm oil fatty acid sarcosine, and the salt thereof includes, for example, a sodium salt, potassium salt, magnesium salt, calcium salt and aluminum salt of the N-acyl sarcosine.

The higher fatty acid ester is a reaction product of a higher fatty acid and alcohol. The number of carbon atoms in the higher fatty acid is preferably 10 to 18. When the number of carbon atoms is less than 10, the resulting higher fatty acid ester is easily volatilized, while when the number of carbon atoms is higher than 18, the promoting effect on transcutaneous absorption may be lowered. The C10 to C18 higher fatty acid includes, for example, saturated aliphatic monocarboxylic acids such as capric acid, lauric acid, myristic acid, palmitic acid and stearic acid; unsaturated aliphatic carboxylic acids such as palmitoleic acid, oleic acid, vaccenic acid, linoleic acid and linolenic acid; and saturated aliphatic dicarboxylic acids such as sebacic acid. The number of carbon atoms in the alcohol is preferably 1 to 20. When the number of carbon atoms is higher than 20, the promoting effect on transcutaneous absorption may be lowered. The C1 to C20 alcohol includes, for example, saturated fatty alcohols such as methyl alcohol, ethyl alcohol, propyl alcohol, isopropyl alcohol, butyl alcohol, isobutyl alcohol, tertiary butyl alcohol, pentyl alcohol, hexyl alcohol, heptyl alcohol, octyl alcohol, capryl alcohol, nonyl alcohol, decyl alcohol, lauryl alcohol, myristyl alcohol, palmityl alcohol and stearyl alcohol.

The higher fatty acid ester of the C10 to C18 higher fatty acid and C1 to C20 alcohol includes, for example, isopropyl myristate, isopropyl palmitate, isopropyl laurate, isopropyl stearate etc.

The number of carbon atoms in the dicarboxylic acid is preferably 2 to 10. When the number of carbon atoms is outside of this range, the promoting effect on transcutaneous absorption may be lowered. The C2 to C10 dicarboxylic acid includes, for example, saturated aliphatic dicarboxylic acids such as oxalic acid, malonic acid, succinic acid, glutaric acid, adipic acid, pimelic acid and suberic acid; unsaturated aliphatic dicarboxylic acids such as fumaric acid and maleic acid; and aromatic dicarboxylic acids such as phthalic acid, isophthalic acid and terephthalic acid. The salt thereof includes, for example, a sodium salt, calcium salt and aluminum salt of the dicarboxylic acid.

The hydroxycarboxylic ester is a reaction product of a hydroxycarboxylic acid and alcohol. The number of carbon atoms in the hydroxycarboxylic acid is preferably 3 to 6. When the number of carbon atoms is less than 3, the resulting hydroxycarboxylic ester is easily volatilized, while when the number of carbon atoms is higher than 6, the promoting effect on transcutaneous absorption may be lowered. The C3 to C6 hydroxycarboxylic acid includes, for example, monocarboxylic acids such as lactic acid and glyceric acid and dicarboxylic acids such as malic acid and tartaric acid. The number of carbon atoms in the alcohol is preferably 1 to 20. When the number of carbon atoms is higher than 20, the promoting effect on transcutaneous absorption may be lowered. The C1 to C20 alcohol includes those used in the higher fatty acid ester described above.

The hydroxycarboxylic ester of the C3 to C6 hydroxycarboxylic acid and C1 to C20 alcohol includes, for example, myristyl lactate, cetyl lactate etc.

The fatty acid ethanol amide includes, for example, lauric acid monoethanol amide, lauric acid diethanol amide, lauroyl monoethanol amide, palmitic acid monoethanol amide, palmitic acid diethahol amide, myristic acid monoethanol amide, myristic acid diethanol amide, lauric acid/myristic acid monoethanol amide, palm oil fatty acid monoethanol amide, palm oil fatty acid diethanol amide, polyoxyethylene-added lauroyl monoethanol amide, and polyoxyethylene-added palm oil fatty acid monoethanol amide.

The mucopolysaccharide includes, for example, hyaluronic acid, chondroitin, chondroitin sulfate, dermatan sulfate, heparan sulfate, heparin, keratan sulfate and pharmacologically acceptable salts thereof.

In particular, the transcutaneous absorption enhancer is more preferably at least one member selected from the group consisting of glycerin, propylene glycol, urea, squalane and mucopolysaccharide.

The amount of the transcutaneous absorption enhancer incorporated into the dermal composition for external use of the present invention is preferably 0.1 to 20,000 parts by weight based on 100 parts by weight of total of sodium cromoglycate and the base. When the content is less than 0.1 part by weight, the sufficient promoting effect on transcutaneous absorption may not be obtained, while when the content is higher than 20,000 parts by weight, skin irritation may appear, and fluidity may become too high, thus making it difficult to keep the preparation form depending on the base. The content is more preferably 10 to 10,000 parts by weight.

The base shall be pharmacologically acceptable, and bases known in the art, such as an ointment, a liniment and a lotion can be used, and examples thereof include polymers such as sodium alginate, propylene glycol alginate, gelatin, corn starch, tragacanth gum, methyl cellulose, hydroxyethyl cellulose, carboxymethyl cellulose, dextrin, carboxymethyl starch, polyvinyl alcohol, polysodium acrylate, methoxy ethylene-maleic anhydride copolymer, polyvinyl ether, and polyvinyl pyrrolidone; fats and oils such as beeswax, olive oil, cacao oil, sesame oil, soybean oil, camellia oil, peanut oil, beef tallow, lard and lanolin; white vaseline; paraffin; gelled hydrocarbons (for example, trade name "Plastibase", manufactured by Bristol-Myers Squibb); higher fatty acids such as stearic acid; higher alcohols such as cetyl alcohol and stearyl alcohol; polyvalent alcohols such as glycerin, propylene glycol and ethylene glycol; polyethylene glycol; surfactants; and water.

The surfactants include, but are not limited to, lecithin derivatives, propylene glycol fatty acid ester, glycerin fatty acid ester, polyoxyethylene glycerin fatty acid ester, polyglycerol fatty acid ester, sorbitan fatty acid ester, polyoxyethylene fatty acid ester, polyoxyethylene sorbitol fatty acid ester, polyoxyethylene alkyl phenyl formaldehyde condensate, polyoxyethylene castor oil/hydrogenated castor oil, polyoxyethylene sterol/hydrogenated sterol, polyethylene glycol fatty acid ester, polyoxyethylene alkyl ether, polyoxyethylene polyoxypropylene alkyl ether, polyoxyethylene lanoline/lanoline alcohol/beeswax derivative, polyoxyethylene alkyl amine/fatty acid amide, polyoxyethylene alkyl ether phosphoric acid/phosphate, and high-molecular emulsifier.

In particular, the water-soluble base is preferably used. The component in the water-soluble base includes, for example, water, glycerin, propylene glycol or a mixture thereof, and water-soluble gel having polyacrylate etc. added to such material.

In addition, an adhesive used conventionally in a plaster and tape can also be used as the base. The adhesive shall be pharmacologically acceptable, and adhesives known in the art can be used, and examples thereof include an acrylic adhesive, rubber-based adhesive, silicon-based adhesive and urethane-based adhesive. In particular, the acrylic adhesive and rubber-based adhesive can be preferably used. These adhesives are in an arbitrary state, for example in the form of a solution, emulsion, hot-melt etc.

The acrylic adhesive includes, for example, adhesives containing polyalkyl (meth)acrylate obtained by copolymerizing alkyl (meth)acrylate as main component, and it may be a copolymer of alkyl (meth)acrylate and a multifunctional monomer copolymerizable therewith or other vinyl monomer.

The alkyl (meth)acrylate includes, for example, 2-ethylhexyl (meth)acrylate, dodecyl (meth)acrylate etc.

The multifunctional monomer includes, for example, 1,6-hexane glycol methacrylate, tetraethylene glycol diacrylate etc., and the other vinyl monomer includes, for example, N-vinyl-2-pyrrolidone, vinyl acetate etc.

The rubber-based adhesive includes adhesives based on natural rubber, a styrene-isoprene-styrene block copolymer or a styrene-olefin-styrene block copolymer, to which a tackifier such as rosin, hydrogenated rosin, rosin ester, terpene resin, terpene phenol resin, petroleum-based resin, coumarone resin, and coumarone-indene resin is generally added.

A wide variety of other efficacious components may be added if necessary to the dermal composition for external use of the present invention. The efficacious components include, but are not limited to, steroid anti-inflammatory agents, non-steroid anti-inflammatory agents, anti-allergy agents, anti-histamine agents, sterilizing agents, antibiotics, immunosuppressive agents etc.

Inorganic fillers such as kaolin, bentonite, zinc oxide and titanium oxide, viscosity regulators, antioxidants, pH adjusting agents, buffers, preservatives and perfumes etc. may be added if necessary to the dermal composition for external use of the present invention.

The pH value of the dermal composition for external use of the present invention is preferably 2 to 7. When the pH is 2 or less, the skin to which it was applied may be irritated or cromoglycic acid may be precipitated, while when the pH is higher than 7, the stability of the monoester of polyvalent alcohol and salicylic acid may be deteriorated. The pH is more preferably 4 to 5.

The method of producing the dermal composition for external use of the present invention is not particularly limited, and there is a method which involves kneading the above-mentioned sodium cromoglycate, the monoester of polyvalent alcohol and salicylic acid, etc., with the base.

The form of the dermal composition for external use of the present invention is not particularly limited, and the composition may be in such a state that the above sodium cromoglycate etc. are dissolved in, or mixed and dispersed in, the base to form a cream, paste, jelly, gel, emulsion or liquid (ointment, liniment, lotion etc.); the above sodium cromoglycate etc. are dissolved in, or mixed and dispersed in, the base and spread on a substrate (poultice etc.); and the above sodium cromoglycate etc. are dissolved in, or mixed and dispersed in, an adhesive as a base and spread on a substrate (plaster, tape etc.).

When the substrate is used, the substrate can be suitably selected depending on the form of the dermal composition for external use, and it is preferably a flexible material through which chemicals such as sodium cromoglycate do not permeate or hardly permeate, and examples thereof include resin films made of cellulose acetate, ethyl cellulose, polyethylene, polyvinyl chloride, vinyl acetate-vinyl chloride copolymer, ethylene-vinyl acetate copolymer, ethylene-vinyl acetate-carbon monoxide copolymer, ethylene-butyl acrylate-carbon monoxide copolymer, polyvinylidene chloride, polyurethane, nylon or polyethylene terephthalate; aluminum sheets; woven fabrics; unwoven fabrics, and laminated sheets thereof.

The dermal composition for external use of the present invention exhibits the high therapeutic effect of sodium cromoglycate by using sodium cromoglycate in combination with the monoester of polyvalent alcohol and salicylic acid.

The dermal composition for external use of the present invention is used for example as cosmetics, pharmaceutical preparations etc. When the composition is used as cosmetics, it is used as face lotion, milky lotion, facial pack etc. When the composition is used as pharmaceutical preparations, it can be used to treat various skin diseases such as rough dry skin, rash, heat rash, sore, frostbite, diaper rash, atopic dermatitis, contact dermatitis, seborrheic dermatitis, lichen simplex chronicus Vidal, nummular eczema, housewife eczema, solar dermatitis, insect bite, pruritus, prurigo, drug eruption, toxicoderma, psoriasis, parapsoriasis, pustulosis palmaris et plantaris, lichen planus, lichen nitidus, pityriasis rubra pilaris Devergie, pityriasis rosea Gibert, erythema, erythrodermia, discoid lupus erythematosus, systemic lupus erythematosus, pemphigus, pemphigoid, dermatitis herpetiformis Duhring, alopecia areata, vitiligo vulgaris, sarcoidosis, cutaneous amyloidosis, keloid, hypertrophic scar, wound, bed sore, skin ulcer, loss of hair, etc.

The present invention also relates to a cosmetic which is obtainable by using the dermal composition for external use of the present invention and a pharmaceutical preparation which is obtainable by using the dermal composition for external use of the present invention.

The method for applying the dermal composition for external use of the present invention is varied depending on the type of disease, the severity of conditions, the size of an affected site, but for example, the composition is applied once or several times onto the affected site in an amount of 0.1 to 10 g per day.

BEST MODE FOR CARRYING OUT THE INVENTION

The present invention is described in more detail by reference to the Examples, but the present invention is not limited to the Examples.

EXAMPLES 1 TO 33 AND COMPARATIVE EXAMPLES 1 TO 16

The respective components shown in Tables 1 to 5 were admixed in predetermined amounts (% by weight) to prepare a gel, a cream or an ointment.

In Tables 1 to 5, the respective components are as follows:

Sodium cromoglycate (DSCG manufactured by Fukuzyu Pharmaceutical Co., LTD.), glycol salicylate (trade name "Saliment", SG manufactured by Yoshitomi Fine Chemicals, Ltd.), a hydrophilic ointment (manufactured by Maruishi Pharmaceutical. Co., Ltd.), white vaseline (manufactured by Maruishi Pharmaceutical. Co., Ltd.), stearyl alcohol (manufactured by Wako Pure Chemical Industries, Ltd.), polyoxyethylene hydrogenated castor oil 60 (trade name "HCO-60", manufactured by Nikko Chemicals Co., Ltd.), polyacrylate gel (trade name "Sintalen L", PA gel manufactured by 3V Sigma Chemical Co.), glycerin (manufactured by Maruishi Pharmaceutical. Co., Ltd.), propylene glycol (PG manufactured by Maruishi Pharmaceutical. Co., Ltd.), alginic acid propylene glycol ester (APG manufactured by Kibun food chemifa Co., Ltd.), urea (manufactured by Kozakai pharmaceutical Co., Ltd.), sodium hyaluronate (HA manufactured by Asahi Kasei Corporation), squalane (manufactured by Maruha Corporation), salicylic acid (SA manufactured by Wako Pure Chemical Industries, Ltd.), methyl salicylate (SM manufactured by Wako Pure Chemical Industries, Ltd.), lauric acid diethanol amide (LD manufactured by NOF Corporation), triethanol amine (Nippon Shokubai Co., Ltd.) and methyl p-oxybenzoate (Paraben manufactured by Yoshitomi Fine Chemicals,Ltd.).

In the base in Tables 3 and 5, "vaseline etc." refers to a mixture of white vaseline:stearyl alcohol: polyoxyethylene hydrogenated castor oil 60=6:1:1 (ratio by weight ).

The gel, cream and ointment prepared in Examples 1 to 33 and Comparative Examples 1 to 16 were used in Test Examples 1 to 6 and evaluated for their effect.

The results are shown in Tables 1 to 5.

TEST EXAMPLE 1

Effect on Primary Irritative Skin Reaction Induced by Dinitrochlorobenzene

Dorsal skin of a 7-week-old male Wister rat was shaved, and 20 μL of 0.8% (w/v) 2,4-dinitrochlorobenzene (DNCB manufactured by Wako Pure Chemical Industries, Ltd.) in acetone was dropped onto the hair-shaved region and then dried.

Then, a circular polyethylene terephthalate/ethylene-vinyl acetate laminate film having a radius of 1 cm was provided on the polyethylene terephthalate side with 0.1 g of the gel, cream or ointment, and then put on so as to bring this side into contact with the hair-shaved region.

Twenty four hours thereafter, the film was released, and the intensity of erythema (B) on the region was measured with a color difference meter (CR-200 manufactured by Minolta). Separately, a control agent (that is, a preparation wherein sodium cromoglycate in the gel, cream or ointment was replaced by the same base composition as in the original gel, cream or ointment) was used in place of the gel, cream or ointment and measured in the same manner for the intensity of erythema (A). From these results, the degree of suppression was calculated from the following equation:

Degree of suppression (%)=((A)−(B))/(A)×100

TEST EXAMPLE 2

Effect on Type IV Allergic Reaction (Skin Contact Hypersensitive Reaction Induced by Dinitrochlorobenzene)

Abdominal skin of a 5-week-old male Wister rat was shaved, and 20 μL of 20% (w/v) 2,4-dinitrochlorobenzene in acetone was dropped onto the hair-shaved region and then dried to sensitize the skin. Two weeks after sensitization, dorsal skin of the rat was shaved, and then, 20 μL of 0.5% (w/v) 2,4-dinitrochlorobenzene in acetone was dropped onto the hair-shaved region and thereafter, dried to induce the reaction.

Then, a circular polyethylene terephthalate/ethylene-vinyl acetate laminate film having a radius of 1 cm was provided on the polyethylene terephthalate side with 0.1 g of the gel, cream or ointment, and then put on so as to bring this side into contact with the hair-shaved region of dorsal skin.

Twenty four hours after the film was put on, the film was released, and the intensity of erythema (B) on the region was measured with a color difference meter (CR-200 manufactured by Minolta). Separately, the control agent in Test Example 1 was used in place of the gel, cream or ointment and measured in the same manner for the intensity of erythema (A). From these results, the degree of suppression was calculated from the following equation:

Degree of suppression (%)=((A)−(B))/(A)×100

TEST EXAMPLE 3

Effect on Type I Allergic Reaction (Homologous PCA Reaction for 48 Hours)

(1) Preparation of Rat Anti-2,4-Dinitrobenzenesulfonic Acid—Ascaris Suum Extract (DNP-As) Serum DNP-As was prepared according to a method of Tada and Okumura (Journal of Immunology, 106, 1002, 1971). That is, an extract of Ascaris suum was prepared according to a method of Strejan and Campbell (Journal of Immunology, 98, 893, 1967) and then bound to 2,4-dinitrobenzenesulfonic acid (DNP) by a method of Eisen et al. (Journal of American Chemical Society, 75, 4583, 1953), whereby DNP-As was obtained.

One mg of DNP-As thus obtained was dissolved in 1 ml of physiological saline containing $10^{10}$ of dead pertussis bacteria floating therein, and then injected into the skin of the extremities of a female rat weighing about 200 g. After 5 days, 0.5 mg of DNP-As was dissolved in 0.5 mL of physiological saline and injected into the right and left dorsal muscles of the rat. Eight days after the initial injection, blood was collected from the aorta abdominals, and se-rum was separated to give rat anti-DNP-As serum.

The titer of this antiserum in rat homologous PCA reaction for 24 hours was 1:512.

(2) Effect on Rat Homologous PCA Reaction for 48 Hours

Dorsal skin of a 7-week-old male Wister rat was shaved, and 0.05 mL of rat anti-DNA-As serum diluted 100-fold with physiological saline was administered intracutaneously for passive sensitization. Immediately thereafter, a circular polyethylene terephthalate/ethylene-vinyl acetate laminate film having a radius of 1 cm was provided on the polyethylene terephthalate side with 0.1 g of the gel, cream or ointment, and then put on so as to bring this side into contact with the hair-shaved region. Twenty hours after sensitization, the gel, cream or ointment was put on in the same manner. Twenty four hours after sensitization, the film was released, and 2.5 mL/kg of 0.5% Evans Blue (manufactured by Merck Ltd.) in physiological saline containing 2 mg/mL of DNP-As as the corresponding antigen was intravenously administered to induce PCA reaction.

The pigment leakage from the site where the intradermal reaction had been induced was extracted and quantified according to a method of Harada et al. (J. Pharm. Pharmacol., 23, 218, 1971). That is, the animal was sacrificed 1 hour after injection of the antigen, and the skin in the PCA reaction site was cut thin and dipped for 24 hours in a mixed solution consisting of 0.3% aqueous sodium sulfate and acetone in a volume ratio 3:7 to determine the amount of the pigment leakage (B). As the control in this test, the control agent in Test Example 1 was used to determine the amount of the pigment leakage (A) in the same manner. From these results, the degree of suppression was calculated from the equation below:

Degree of suppression (%)=((A)−(B))/(A)×100

TEST EXAMPLE 4

Effect on a Rat Dry Skin Model by Using N-lauroyl Sarcosine-dinitrochlorobenzene N-lauroyl sarcosine (manufactured by Nacalai Tesque, Inc.) and gelled hydrocarbons (trade name "Plastibase", manufactured by Bristol-Myers Squibb) were fed in a weight ratio of 2:98 to a mortar and kneaded until the mixture was uniform as a whole to give an ointment (referred to hereinafter as Plastibase ointment containing 2% LS).

Dorsal skin of a 7-week-old male Wister rat was shaved, and a circular polyethylene terephthalate/ethylene-vinyl acetate laminate film having a radius of 1 cm was provided on the polyethylene terephthalate side with 0.1 g of Plastibase ointment containing 2% LS, and then put on so as to bring this side into contact with the hair-shaved region.

Twenty four hours thereafter, the film was released, and 20 μL of 1% (w/v) 2,4-dinitrochlorobenzene in acetone was applied onto this site and then well dried. Immediately after drying, a circular polyethylene terephthalate/ethylene-vinyl acetate laminate film having a radius of 1 cm was provided on the polyethylene terephthalate side with 0.1 g of the gel, cream or ointment, and then put on so as to bring this side into contact with the hair-shaved region.

Eighteen hours after the film was put on, the firm was released, and 6 hours thereafter, the transepidermal water loss (TEWL) in the site was measured with EVAPORIM-ETER EP1 (manufactured by Servomed Co.,). Lower TEWL is indicative of a higher therapeutic effect on dry skin. Separately, the ointment base (Plastibase) only was used as the control in place of the gel, cream or ointment and examined in the same manner. The normal rat skin (skin onto which neither Plastibase ointment containing 2% LS nor the DNCB solution in acetone had been applied), without previously sticking thereon or after sticking only the ointment base (Plastibase) thereon for 24 hours was measured for TEWL in the same manner.

Test Example 5

Effect on a Rat Model with Reduction in Skin Barrier Functions by Using N-lauroyl Sarcosine-dinitrochlorobenzene Crystal Violet (manufactured by Wako Pure Chemical Industries, Ltd.) and a hydrophilic ointment were fed in a weight ratio of 1:99 to a mortar and kneaded until the mixture was uniform as a whole to give an ointment (referred to hereinafter as the hydrophilic ointment containing 1% CV).

Dorsal skin of a 7-week-old male Wister rat was shaved, and a circular polyethylene terephthalate/ethylene-vinyl acetate laminate film having a radius of 1 cm was provided on the polyethylene terephthalate side with 0.1 g of Plastibase ointment containing 2% LS, and then put on so as to bring this side into contact with the hair-shaved region.

Twenty four hours after the film was put on, the film was released, and 20 μL of 1% (w/v) 2,4-dinitrochlorobenzene in acetone was applied onto this site and then well dried. Immediately after drying, a circular polyethylene terephthalate/ethylene-vinyl acetate laminate film having a radius of 1 cm was provided on the polyethylene terephthalate side with 0.1 g of the gel, cream or ointment, and then put on so as to bring this side into contact with the hair-shaved region.

Twenty four hours after the film was put on, the film was released, and a circular polyethylene terephthalate/ethylene-vinyl acetate laminate film having a radius of 1 cm was provided on 0.05 g of the hydrophilic ointment containing 1% CV, and then put on so as to bring this side into contact with the hair-shaved region.

Twenty four hours after the film was put on, the film was released, and the hair-shaved region was subjected to 8 times of tape stripping with a cellophane tape (manufactured by Sekisui Chemical Co., Ltd.) to remove its keratin layer, and the bluing degree of that site (B) was measured with a color difference meter. As the control in this test, the control agent in Test Example 1 was used to determine bluing degree (A) in the same manner. From these results, the degree of suppression was calculated from the equation below. A higher bluing degree indicates a higher amount of Crystal Violet entering the epidermal layer, thus showing a reduction in skin barrier functions, and suppression of the bluing degree indicates that skin barrier functions are improved, that is, the skin is kept in a healthy condition.

Degree of suppression $(\%) = ((A) - (B))/(A) \times 100$

TEST EXAMPLE 6

The preparations in Examples 28 to 33 were stored at 60° C. for 4 weeks, and before and after storage, the concentrations of sodium cromoglycate and glycol salicylate in the preparations were measured by high performance liquid chromatography.

TABLE 1

| | Composition (% by weight) | | | | | | | | | Evaluation | | | | |
| | | | | | | | | | | Test Example 1 | Test Example 2 | Test Example 3 | Test Example 4 | Test Example 5 |
| | | | Base | | Transcutaneous absorption enhancer | | | | Preservative | degree of suppression (%) | degree of suppression (%) | degree of suppression (%) | TEWL $(g/m^2 \cdot h)$ | degree of suppression (%) |
| | DSCG | SG | Water | PA gel | APG | Glycerin | PG | Urea | HA | Paraben | | | | | |
| Example 1 | 5 | 15 | 25 | 0 | 0 | 30 | 25 | 0 | 0 | 0 | 70.1 | 66.0 | 25 | 7 | 68.2 |
| Example 2 | 5 | 15 | 20 | 0 | 0 | 30 | 25 | 5 | 0 | 0 | 71.8 | 69.1 | 28.9 | 6 | 70.1 |
| Example 3 | 5 | 15 | 24.8 | 0 | 0 | 30 | 25 | 0 | 0.2 | 0 | 72.9 | 69.5 | 29.2 | 6 | 70.5 |
| Example 4 | 5 | 15 | 24 | 1 | 0 | 30 | 25 | 0 | 0 | 0 | 70.3 | 65.8 | 24.8 | 7 | 69.0 |
| Example 5 | 5 | 15 | 19 | 1 | 0 | 30 | 25 | 5 | 0 | 0 | 72.1 | 69.0 | 29.5 | 6 | 70.5 |
| Example 6 | 5 | 15 | 23.8 | 1 | 0 | 30 | 25 | 0 | 0.2 | 0 | 73.0 | 70.1 | 29.1 | 6 | 71.1 |
| Example 7 | 5 | 15 | 23.5 | 1 | 0 | 30 | 25 | 0 | 0 | 0.5 | 73.0 | 70.0 | 30.0 | 6 | 70.8 |
| Example 8 | 5 | 15 | 23.3 | 1 | 0 | 30 | 25 | 0 | 0.2 | 0.5 | 72.9 | 73.2 | 30.3 | 6 | 71.5 |
| Example 9 | 5 | 15 | 22.5 | 1 | 1 | 30 | 25 | 0 | 0 | 0.5 | 73.3 | 73.0 | 30.5 | 6 | 71.6 |
| Example 10 | 5 | 15 | 22.3 | 1 | 1 | 30 | 25 | 0 | 0.2 | 0.5 | 73.5 | 73.5 | 30.8 | 6 | 72.0 |

TABLE 2

| | Composition (% by weight) | | | | | | | | Evaluation | |
| --- | --- | --- | --- | --- | --- | --- | --- | --- | --- | --- |
| | | | Base | | | | | | Test Example 1 | Test Example 4 |
| | | | Hydrophilic | Transcutaneous absorption enhancer | | | | | degree of suppression | TEWL |
| | DSCG | SG | ointment | Glycerin | PG | Urea | HA | Squalane | (%) | (g/m² · h) |
| Example 11 | 5 | 15 | 80 | 0 | 0 | 0 | 0 | 0 | 41.2 | 14 |
| Example 12 | 5 | 15 | 50 | 30 | 0 | 0 | 0 | 0 | 51.3 | 10 |
| Example 13 | 5 | 15 | 50 | 0 | 30 | 0 | 0 | 0 | 50 | 11 |
| Example 14 | 5 | 15 | 75 | 0 | 0 | 5 | 0 | 0 | 50.9 | 10 |
| Example 15 | 5 | 15 | 79.8 | 0 | 0 | 0 | 0.2 | 0 | 49.6 | 9 |
| Example 16 | 5 | 15 | 65 | 0 | 0 | 0 | 0 | 15 | 49.6 | 11 |
| Example 17 | 5 | 15 | 35 | 30 | 0 | 0 | 0 | 15 | 63 | 7 |
| Example 18 | 5 | 15 | 30 | 30 | 0 | 5 | 0 | 15 | 65.1 | 7 |
| Example 19 | 5 | 15 | 30 | 0 | 30 | 5 | 0 | 15 | 62.7 | 8 |

TABLE 3

| | Composition (% by weight) | | | | | | | | | Evaluation | |
| --- | --- | --- | --- | --- | --- | --- | --- | --- | --- | --- | --- |
| | | | Base | | Transcutaneous absorption enhancer | | | | | Test Example 1 degree of suppression | Test Example 4 TEWL |
| | DSCG | SG | Vaseline etc. | Water | Glycerin | PG | Urea | HA | Squalane | (%) | (g/m² · h) |
| Example 20 | 5 | 15 | 40 | 40.0 | 0 | 0 | 0 | 0 | 0 | 40.1 | 16 |
| Example 21 | 5 | 15 | 40 | 30.0 | 10 | 0 | 0 | 0 | 0 | 48.6 | 12 |
| Example 22 | 5 | 15 | 40 | 30.0 | 0 | 10 | 0 | 0 | 0 | 47.9 | 12 |
| Example 23 | 5 | 15 | 40 | 35.0 | 0 | 0 | 5 | 0 | 0 | 47.0 | 12 |
| Example 24 | 5 | 15 | 40 | 39.8 | 0 | 0 | 0 | 0.2 | 0 | 46.0 | 11 |
| Example 25 | 5 | 15 | 40 | 25.0 | 0 | 0 | 0 | 0 | 15 | 46.5 | 13 |
| Example 26 | 5 | 15 | 40 | 10.0 | 10 | 0 | 5 | 0 | 15 | 62.9 | 8 |
| Example 27 | 5 | 15 | 40 | 10.0 | 0 | 10 | 5 | 0 | 15 | 61.0 | 10 |

TABLE 4

| | Composition (% by weight) | | | | | | | | | | | Evaluation | | | |
| --- | --- | --- | --- | --- | --- | --- | --- | --- | --- | --- | --- | --- | --- | --- | --- |
| | | | Base | | Transcutaneous absorption enhancer | | | Preservative | pH adjusting agent | | | Test Example 1 degree of suppression (%) | Test Example 4 TEWL (g/m²·h) | Test Example 6 Residual degree (%) | |
| | DSCG | SG | Water | PA gel | Glycerin | PG | HA | Paraben | Triethanol amine | pH | | | | DSCG | SG |
| Example 28 | 5 | 15 | 23.5 | 1 | 30 | 25 | 0 | 0.5 | Optimal amount | 4.0 | | 71.8 | 6 | 99.5 | 98.7 |
| Example 29 | 5 | 15 | 23.5 | 1 | 30 | 25 | 0 | 0.5 | Optimal amount | 4.5 | | 72.1 | 6 | 99.6 | 98.4 |
| Example 30 | 5 | 15 | 23.5 | 1 | 30 | 25 | 0 | 0.5 | Optimal amount | 5.0 | | 72.0 | 6 | 99.2 | 98.0 |
| Example 31 | 5 | 15 | 23.3 | 1 | 30 | 25 | 0.2 | 0.5 | Optimal amount | 4.0 | | 72.8 | 6 | 99.6 | 98.9 |
| Example 32 | 5 | 15 | 23.3 | 1 | 30 | 25 | 0.2 | 0.5 | Optimal amount | 4.5 | | 72.9 | 6 | 99.6 | 98.5 |
| Example 33 | 5 | 15 | 23.3 | 1 | 30 | 25 | 0.2 | 0.5 | Optimal amount | 5.0 | | 73.1 | 6 | 99.3 | 98.0 |

TABLE 5

| | Composition (% by weight) | | | | | | | | | | | | |
| --- | --- | --- | --- | --- | --- | --- | --- | --- | --- | --- | --- | --- | --- |
| | | | | Base | | | | | Transcutaneous absorption enhancer | | | | Preservative |
| | DSCG | SA | SM | Hydrophilic ointment | Vaseline etc. | Water | PA gel | LD | Glycerin | PG | Squalane | Urea | Paraben |
| Comparative Example 1 | 5 | 0 | 0 | 0 | 0 | 95 | 0 | 0 | 0 | 0 | 0 | 0 | 0 |

TABLE 5-continued

| | | | | | | | | | | | | | |
|---|---|---|---|---|---|---|---|---|---|---|---|---|---|
| Comparative Example 2 | 5 | 15 | 0 | 0 | 0 | 79 | 1 | 0 | 0 | 0 | 0 | 0 | 0 |
| Comparative Example 3 | 5 | 0 | 15 | 0 | 0 | 79 | 1 | 0 | 0 | 0 | 0 | 0 | 0 |
| Comparative Example 4 | 5 | 0 | 0 | 0 | 0 | 38.5 | 1 | 0 | 30 | 25 | 0 | 0 | 0.5 |
| Comparative Example 5 | 5 | 15 | 0 | 0 | 0 | 23.5 | 1 | 0 | 30 | 25 | 0 | 0 | 0.5 |
| Comparative Example 6 | 5 | 0 | 15 | 0 | 0 | 23.5 | 1 | 0 | 30 | 25 | 0 | 0 | 0.5 |
| Comparative Example 7 | 5 | 0 | 0 | 95 | 0 | 0 | 0 | 0 | 0 | 0 | 0 | 0 | 0 |
| Comparative Example 8 | 5 | 15 | 0 | 80 | 0 | 0 | 0 | 0 | 0 | 0 | 0 | 0 | 0 |
| Comparative Example 9 | 5 | 0 | 15 | 80 | 0 | 0 | 0 | 0 | 0 | 0 | 0 | 0 | 0 |
| Comparative Example 10 | 5 | 0 | 0 | 50 | 0 | 0 | 0 | 0 | 30 | 0 | 15 | 0 | 0 |
| Comparative Example 11 | 5 | 15 | 0 | 35 | 0 | 0 | 0 | 0 | 30 | 0 | 15 | 0 | 0 |
| Comparative Example 12 | 5 | 0 | 15 | 35 | 0 | 0 | 0 | 0 | 30 | 0 | 15 | 0 | 0 |
| Comparative Example 13 | 5 | 0 | 0 | 0 | 40 | 55 | 0 | 0 | 0 | 0 | 0 | 0 | 0 |
| Comparative Example 14 | 5 | 15 | 0 | 0 | 40 | 40 | 0 | 0 | 0 | 0 | 0 | 0 | 0 |
| Comparative Example 15 | 5 | 0 | 15 | 0 | 40 | 40 | 0 | 0 | 0 | 0 | 0 | 0 | 0 |
| Comparative Example 16 | 5 | 0 | 0 | 0 | 0 | 42 | 1 | 2 | 30 | 0 | 0 | 20 | 0 |
| Control Normal skin | With the ointment base (Plastibase) stuck thereon | | | | | | | | | | | | |
| Normal skin | With nothing stuck thereon | | | | | | | | | | | | |
| Normal skin | With the ointment base (Plastibase) stuck thereon | | | | | | | | | | | | |

| | Evaluation | | | |
|---|---|---|---|---|
| | Test Example 1 degree of suppression (%) | Test Example 2 degree of suppression (%) | Test Example 3 degree of suppression (%) | Test Example 4 TEWL (g/m² · h) |
| Comparative Example 1 | 4.8 | 4.5 | 2.0 | 39 |
| Comparative Example 2 | 4.5 | 4.6 | 2.2 | 40 |
| Comparative Example 3 | 4.5 | 4.3 | 2.4 | 40 |
| Comparative Example 4 | 4.3 | 4.5 | 2.2 | 38 |
| Comparative Example 5 | 4.7 | 4.0 | 2.2 | 37 |
| Comparative Example 6 | 4.7 | 4.1 | 1.8 | 38 |
| Comparative Example 7 | 5.0 | 4.2 | 1.9 | 39 |
| Comparative Example 8 | 4.8 | 3.9 | 2.3 | 40 |
| Comparative Example 9 | 4.8 | 4.0 | 2.0 | 40 |
| Comparative Example 10 | 4.0 | 4.0 | 2.4 | 41 |
| Comparative Example 11 | 4.4 | 4.0 | 2.1 | 39 |
| Comparative Example 12 | 4.3 | 3.8 | 1.6 | 40 |
| Comparative Example 13 | 4.6 | 3.8 | 2.0 | 39 |
| Comparative Example 14 | 3.9 | 3.9 | 2.5 | 41 |
| Comparative Example 15 | 3.9 | 3.9 | 2.1 | 40 |
| Comparative Example 16 | 29.4 | 26.8 | 8.7 | 18 |
| Control | — | — | — | 41 |
| Normal skin | — | — | — | 3 |
| Normal skin | — | — | — | 4 |

From the results of the degree of suppression in Test Example 1 shown in Tables 1 to 5, it was found that the dermal composition for external use of the present invention demonstrates a sufficient effect in treatment of the skin inflammation. From the results of the degree of suppression in Test Example 2 shown in Tables 1 and 5, it was found that the dermal composition for external use of the present invention demonstrates a sufficient effect in treatment of the skin inflammation in which type IV allergy is involved. From the results of the degree of suppression in Test Example 3 shown in Tables 1 and 5, it was found that the dermal composition for external use of the present invention demonstrates a sufficient effect in treatment of the skin inflammation in which type I allergy is involved. From the TEWL values in Test Example 4 shown in Tables 1 to 5, it was found that the dermal composition for external use of the present invention demonstrates a sufficient effect in treatment of dry skin. From the results of the degree of suppression in Test Example 5 shown in Table 1, it was found that the dermal composition for external use of the present invention has an effect of improving the skin barrier functions. From the results in Test Example 6 shown in Table 4, it was found that the dermal composition for external use of the present invention exhibits sufficient shelf stability.

INDUSTRIAL APPLICABILITY

According to the present invention, there can be provided a dermal composition for external use which keeps the skin healthy and demonstrates a sufficient effect in treating skin diseases.

The invention claimed is:

1. A dermal composition for external use, which comprises sodium cromoglycate and a monoester of polyvalent alcohol and salicylic acid contained in a base.

2. The dermal composition for external use according to claim 1 wherein the content of glycol salicylate is 1 to 20% by weight.

3. The dermal composition for external use according to claim 1, wherein the transcutaneous absorption enhancer is at least one member selected from the group consisting of glycerin, propylene glycol, urea, squalane and mucopolysaccharide.

4. The dermal composition for external use according to claim 1, wherein the base is a water-soluble base.

5. The dermal composition for external use according to claim 1, wherein a pH value thereof is of 2 to 7.

6. The dermal composition for external use according to claim 1, wherein a pH value thereof is 4 to 5.

7. A cosmetic, which is obtainable by using the dermal composition for external use according to claim 1.

8. A pharmaceutical preparation, which is obtainable by using the dermal composition for external use according to claim 1.

9. The dermal composition for external use according to claim 2, wherein said dermal composition for external use contains at least one transcutaneous absorption enhancer selected from the group consisting of N-acyl sarcosine or a salt thereof, a higher fatty acid ester of a C10 to C18 higher fatty acid and a C1 to C20 alcohol, a C2 to C10 dicarboxylic acid or a salt thereof, a hydroxycarboxylic ester of a C3 to C6 hydroxycarboxylic acid and a C1 to C20 alcohol, a fatty acid ethanol amide, glycerin, propylene glycol, polyethylene glycol, urea, glycyrrhizinic acid, squalane and mucopolysaccharide.

10. The dermal composition for external use according to claim 2, wherein the base is a water-soluble base.

11. The dermal composition for external use according to claim 2, wherein a pH value thereof is of 2 to 7.

12. The dermal composition for external use according to claim 2, wherein a pH value thereof is 4 to 5.

* * * * *